US008530223B2

(12) United States Patent
Biermann et al.

(10) Patent No.: US 8,530,223 B2

(45) Date of Patent: Sep. 10, 2013

(54) **METHOD TO GROW *LAWSONIA INTRACELLULARIS* BACTERIA IN PERSISTENTLY INFECTED MCCOY CELLS**

(75) Inventors: Yvonne Maria Johanna Corina Biermann, Boxmeer (NL); Carla Christina Schrier, Boxmeer (NL); Petrus Theodorus Johannes Andries Gelder van, Boxmeer (NL); Bram Verdellen, Boxmeer (NL); Barry Lijsdonk, Boxmeer (NL)

(73) Assignee: Intervet International B.V., Boxmeer (NL)

( * ) Notice: Subject to any disclaimer, the term of this patent is extended or adjusted under 35 U.S.C. 154(b) by 0 days.

(21) Appl. No.: 13/505,667

(22) PCT Filed: Nov. 8, 2010

(86) PCT No.: PCT/EP2010/066987

§ 371 (c)(1), (2), (4) Date: May 2, 2012

(87) PCT Pub. No.: WO2011/054951

PCT Pub. Date: May 12, 2011

(65) Prior Publication Data

US 2012/0213739 A1 Aug. 23, 2012

Related U.S. Application Data

(60) Provisional application No. 61/259,465, filed on Nov. 9, 2009.

(30) Foreign Application Priority Data

Nov. 9, 2009 (EP) .................................... 09175372

(51) Int. Cl.
*C12N 1/20* (2006.01)
*A61P 31/04* (2006.01)

(52) U.S. Cl.
USPC ...................................................... 435/252.1

(58) Field of Classification Search
USPC ...................................................... 435/252.1
See application file for complete search history.

(56) References Cited

U.S. PATENT DOCUMENTS 5,885,823 A * 3/1999 Knittel et al. ................ 435/243

FOREIGN PATENT DOCUMENTS

| | | | |
|---|---|---|---|
| DE | EP1609870 | * | 6/2004 |
| EP | 0 843 818 | B1 | 2/2005 |
| WO | 2006/056853 | A1 | 6/2006 |
| WO | 2009/088878 | A1 | 7/2009 |
| WO | 2009/144088 | A2 | 12/2009 |

OTHER PUBLICATIONS

Masters et al., Changing medium and passaging cell lines, Nature Protocols, (2007) vol. 2, No. 9, pp. 2276-2284.*

McOrist et al., Entry of the bacterium ileal symbiont intracellularis into cultured enterocytes and its subsequent release, Research in Veterinary Science (1995) 59: 255-260.*

Smith et al., Lawsonia intracellularis: getting inside the pathogenesis of proliferation enteropathy, Veterinary Microbiology, 82 (2001) 331-345.*

Kennedy et al., "Strategies for improving fermentation medium performance: a review", Journal of Industrial Microbiology & Biotechnology, 1999, pp. 456-475, vol. 23.

International Search Report for corresponding PCT Application No. PCT/EP2010/066987, dated Dec. 28, 2010.

* cited by examiner

*Primary Examiner* — Karen Cochrane Carlson
*Assistant Examiner* — Jennifer M. H. Tichy

(57) ABSTRACT

The present invention pertains to a method to obtain McCoy cells persistently infected with *Lawsonia intracellularis* bacteria, comprising infecting McCoy cells with *Lawsonia intracellularis* bacteria, growing the infected McCoy cells in a suitable medium at an oxygen concentration less than 18% to arrive at a culture of McCoy cells infected with *Lawsonia intracellularis* bacteria, passing at least a part of the said culture to fresh medium, and without adding uninfected McCoy cells to the medium, growing the infected McCoy cells contained in the said at least part in the fresh medium at an oxygen concentration less than 18%, to obtain the persistently infected McCoy cells. The invention also pertains to the use of such persistently infected cells to grow and obtain these bacteria in purified form.

3 Claims, No Drawings

METHOD TO GROW *LAWSONIA INTRACELLULARIS* BACTERIA IN PERSISTENTLY INFECTED MCCOY CELLS

CROSS-REFERENCE TO RELATED APPLICATIONS

This application is a national stage entry under 35 U.S.C. 4371 of PCT/EP2010/066987, filed on Nov. 8, 2010, which claims priority to U.S. Provisional Application No. 61/259,465, filed on Nov. 9, 2009, and EP Application No. 09175372.3, filed on Nov. 9, 2009. The content of PCT/EP2010/066987 is hereby incorporated by reference in its entirety.

The present invention pertains to the growth of the obligate intracellular bacterium *Lawsonia intracellularis*, and its use for the manufacture of a medicament, in particular a vaccine, to treat an infection with *Lawsonia intracellularis* bacteria.

BACKGROUND OF THE INVENTION

*Lawsonia intracellularis* (also called *Lawsonia*) is the causative agent of proliferative enteropathy (also called enteritis or ileitis) in many animals, in particular pigs, and presents a clinical sign and pathological syndrome with mucosal hyperplasia of immature crypt epithelial cells, primarily in the terminal ileum. Other sites of the intestines that can be affected include the jejunum, caecum and colon. Weanling and young adult pigs are principally affected with typical clinical manifestation of rapid weight loss and dehydration. Natural clinical disease in pigs occurs worldwide. The disease is consistently associated with the presence of intracellular curved bacteria, presently known as *Lawsonia intracellularis*. In general, vaccination against *Lawsonia* intracellularis has shown to be an economically efficient measure to treat an infection with *Lawsonia intracellularis*. This way Ileitis can be controlled which allows a better exploitation of the genetic growth potential of the pig. At present there is only one vaccine on the market to protect against *Lawsonia intracellularis*, viz. Enterisol® Ileitis marketed by Boehringer Ingelheim. This vaccine is a live vaccine for oral administration. Other vaccines have also been described but are not commercially available. In any case, for commercial production of substantive volumes of a vaccine to treat an infection with *Lawsonia intracellularis* it would be desirable to have an efficient and economically attractive cultivation method for these intracellular bacteria.

From EP 843 818 a method is known to grow *Lawsonia intracellularis* bacteria in McCoy cells adhered to a substrate (such as a flask bottom or micro-carriers). Indeed, McCoy cells have proven to be adequate host cells to cultivate *lawsonia intracellularis* bacteria. It is also known from this patent that for passage of a culture to actually grow the *Lawsonia intracelluaris* bacteria (i.e. to increase the net number of viable bacteria), one needs to incubate fresh uninfected McCoy cells at low oxygen, that is below 18%, whereafter these fresh cells are inoculated with already infected McCoy cells. Passage to fresh McCoy cells is believed to be necessary since the infected McCoy host cells are ultimately killed by the intracellular *Lawsonia* bacteria. Indeed, it has been described that a *Lawsonia* infection spreads via host cells that lyse and therewith release the intracellular bacteria such that they become available for infection of other cells. A disadvantage of the known method is that at passage, the fresh cells have to be infected. This is a critical step, which takes a relatively long period of time (typically from 6 days up to two weeks but possibly even longer than that) and has a relatively high degree of uncertainty towards success. Due to these typical issues, additional infection steps therefore increase the costs of *Lawsonia intracellularis* cultivation significantly. Moreover, with every additional infection step *Lawsonia intracellularis* may acquire a higher level of attenuation. This makes the known cultivation technique less attractive for the production of bacteria for use in vaccines. Indeed, these disadvantages have been recognized in the art and therefore in WO 2009/088878 infected McCoy cells are not passed to fresh (uninfected) McCoy cells for growing *Lawsonia intracellularis* bacteria. Rather, infected McCoy cells are grown until full infection and then harvested. This way, the repeated infection step when passing the infected McCoy cells can be avoided.

SUMMARY OF THE INVENTION

Still there is a need for an improved cultivation technique for *Lawsonia intracellularis* bacteria. To this end a method to obtain McCoy cells persistently infected with *Lawsonia intracellularis* bacteria has been devised, comprising the steps of infecting McCoy cells with *Lawsonia intracellularis* bacteria, growing the infected McCoy cells in a suitable medium at an oxygen concentration less than 18% to arrive at a culture of McCoy cells infected with *Lawsonia intracellularis* bacteria, passing at least a part of the said culture to fresh medium, and without adding uninfected McCoy cells to the medium, growing the infected McCoy cells contained in the said at least part in the fresh medium at an oxygen concentration less than 18%, to obtain the persistently infected McCoy cells.

Surprisingly it has been found, when infected McCoy cells are grown in a medium and environment that supports growth of the McCoy cells as well as the *Lawsonia intracellularis* bacteria, thereafter passed to fresh medium that does not contain uninfected McCoy cells, and again grown in such a medium and environment, that the McCoy cells remain infected while growing. Against the prior art teachings, repeated infection steps can be dispensed with which not only makes cultivation of the intracellular bacterium relatively simple, but also decreases the risk of over-attenuation (loss of adequate immunogenic properties). Based on the present results it is believed that infected McCoy cells divide into multiple infected cells. This believe is based on the present finding that the McCoy cells as well as the *Lawsonia* bacteria grow without any additional infection steps. It may thus be that the *Lawsonia* bacteria do not need to leave infected cells to infect other McCoy host cells. However, it is not excluded that the latter process additionally takes place since in the supernatant of a culture of persistently infected McCoy cells, extra cellular *Lawsonia* bacteria can be found. It also noted that some infected McCoy cells may not survive the *Lawsonia* infection. However, when using the present invention, a net increase in viable infected McCoy cells can be obtained, which is referred to as McCoy cells being persistently infected.

It is noted that many media are known that support the growth of McCoy cells as well as *Lawsonia intracellularis* bacteria. Generally speaking, it is commonly known how to constitute a medium that supports growth of cells or bacteria. For cells, classical culture media were originally developed by Eagle, Ham and others in the 1950's and 60's. They found that a medium which fulfils the basic needs for growth should comprise inorganic salts, a nitrogen source (for example in the form of nitrogen containing compounds such as peptides or proteins), a carbon source and vitamins. The media are advantageously buffered to prevent them from becoming either too acidic or too alkaline. Within this basic recipe, many different constitutions are available. For example, one could opt for animal derived components to provide the amino acids, but one could also choose for chemically defined amino acids. For the other compounds also numerous variations are possible. To cultivate bacteria even less requirements are necessary. In short, to constitute a medium that supports growth of cells or bacteria is relatively simple. However, optimisation of growth and/or metabolite production can take some development time, in particular when a medium is preferred that is free of serum or other animal derived components. Strategies for improving fermentation medium performance however are commonly known in the art and elaborately described in literature (see for example a review article by Kennedy and Krouse in the Journal of Industrial Microbiology & Biotechnology (1999) 23, 456-475). A medium as simple as the commonly known DMEM may be sufficient to apply the present invention. The environment is also not very critical, although an oxygen concentration below 18% (that is below the oxygen concentration in balance with normal atmospheric oxygen) is necessary to obtain adequate growth of *Lawsonia intracellularis* bacteria.

It is also noted that passing culture cells (also referred to as passaging) is a completely different physiological process than merely adding fresh medium to cells in an existing culture. Adding fresh medium to an existing culture (for example such as known from WO 2006/056853, example 1) is done merely to provide nutrients to enable the existing cells to grow until confluency and stay alive. Passing means that cells are re-seeded in a new culture medium, typically by removing the cells from their substrate and bringing them over in a new culture vessel with a new, blank substrate to which the cells can attach.

The present invention also pertains to the use of McCoy cells persistently infected with *Lawsonia intracellularis* bacteria to grow and obtain these bacteria in purified form. Applicant recognised that persistently infected McCoy cells are very convenient for cultivating the *Lawsonia* bacteria since the infection remains without needing any additional infection steps. The invention also pertains to a McCoy cell line which is persistently infected with *Lawsonia intracellularis* bacteria. It has been found that such cells remain viable even when frozen (in particular at around −196° C.) and subsequently thawed, and that the infection remains persistent even after multiple freeze-thaw cycles. The invention also pertains to the use of this cell line to grow *Lawsonia intracellularis* bacteria for the manufacture of a medicament containing these bacteria (for example a product such as the live vaccine Enterisol Ileitis, commercially available from Boehringer Ingelheim) or a derivative thereof (such as an extract, a subunit, a bacterin, a lysate etc. derived directly from these bacteria by chemical and/or physical treatment; such as for example the vaccines known from International Application PCT/EP2009/054516, assigned to Intervet International BV, which application is incorporated herein by reference) to treat an infection with *Lawsonia intracellularis* bacteria.

DEFINITIONS

McCoy Cell: a fibroblast of mouse origin

Passing: to re-seed cultured cells into fresh medium, in order to support continuous growth of the cells Persistently Infected: to be able and remain infected for an indefinitely long time without requiring repeated infection Suitable Medium: medium suitable to maintain viable cells and to allow growing of the cells Fresh Medium: medium that has sufficient nutrients to sustain growth of cells or micro-organisms To Grow (cells including bacteria): net increase in the amount of viable cells Growth Phase: phase during cultivation in which there is a net increase in viable cells (or bacteria), for example an exponential growth phase or log phase Suspension of Cells: a state wherein the cells are present in a medium without being adhered to a surface To Purify: to increase the concentration, for example by removing impurities or decreasing the relative content of medium To Treat an Infection: to at least aid in preventing, ameliorating or curing an infection or the disease or disorder arising from that infection

EMBODIMENTS OF THE INVENTION

In an embodiment the McCoy cells are grown while being adhered to a surface. It has been found that the present invention works particularly well when the McCoy cells are adhered to a surface such as the bottom of a cultivation flask, plates of a cell factory, micro carrier beads etc. It has also been found that the present invention is very suitable for McCoy cells that are grown while being in suspension. Suspension of the cells has the advantage that a state of confluency (of a surface) is inherently avoided, and thus, the culturing of the infected McCoy cells may continue indefinitely without the need to transfer infected cells from one surface to another. In particular in case of suspension cultivation, the present invention may lead to a continuous cultivation technique instead of batch wise cultivation as known from the prior art. This would not have been possible based on prior art knowledge. In the prior art it has been described that for infection from McCoy cell to McCoy cell the host cell lyses, whereafter the released *Lawsonia* bacteria may infect new cells. Such an infection however is believed to be very difficult in unpolarised (non-attached) McCoy cells. Hence the method in EP 843 818 and numerous subsequent publications from the same research group, which rely on attached McCoy cells, or the method as known from WO 2009/088878 which dispenses with additional infection steps when infected McCoy cells are in suspension for growth of the *Lawsonia intracellularis* bacteria. The present embodiment therefore is in complete contrast with the prior art teachings. It is noted that in the present invention, in either of the embodiments described supra, one could combine adherent growth with suspension growth, for example in subsequent or concurrent cultivation steps.

In another embodiment, passing takes place when the infected McCoy cells are in a growth phase. Applicant found that cultivation is very adequate when passing takes place at a point in time wherein the McCoy cells are still growing. Apparently, when a steady state is reached the McCoy cells may reach some sort of a numb state which cannot be left instantly. It may be that such a state has in the past been confused with a state wherein the McCoy cells are no longer viable. However, before infected McCoy cells lose viability, they can still leave the numb state and start to grow again, for example when being passed to fresh medium. However, this may take some time, which makes the use of infected McCoy cells in such a state less preferred. Preferably, the infected McCoy cells are in an exponential growth phase at passing. This has proven to lead to a very favourable cultivation method in respect of cultivation speed and growth factor (increase of viable infected cells with respect to the number of cells present initially).

In an embodiment of the use according to the present invention, viz. the use of McCoy cells persistently infected with *Lawsonia intracellularis* bacteria to grow and obtain these bacteria in purified form, the use comprises the steps of growing the persistently infected McCoy cells in a suitable medium at an oxygen concentration less than 18% to arrive at a first culture of McCoy cells infected with *Lawsonia intracellularis* bacteria, harvesting at least a part of the first culture to obtain a first batch of *Lawsonia intracellularis* bacteria, passing another part of the first culture to fresh medium, growing the infected McCoy cells contained in the said another part of the culture in the fresh medium at an oxygen concentration less than 18%, to arrive at a second culture of infected McCoy cells, and harvesting at least a part of the second culture to obtain a second batch of *Lawsonia intracellularis* bacteria. In this embodiment a substantially continuous cultivation method is employed, based on the present invention of persistently infected McCoy cells. In this embodiment the infected McCoy cells are grown, for example until growth speed of the infected McCoy cells starts to decrease noticeably. Then, a part of the culture is harvested, typically the main part up to for example 90% of the culture, to obtain the *Lawsonia* bacteria for further use. The remaining part of the culture is passed to fresh medium, for example by simply adding new medium to the cultivation vessel. This remaining part then, containing a relatively small amount of persistently infected McCoy cells, is then allowed to re-grow. After sufficient growth, for example again up to a moment when the growth speed of the infected McCoy cells starts to decrease noticeably again, a second harvest step may take place, and also, a remaining part may be re-grown again to fill the cultivation vessel.

Preferably, at passing the said another (remaining) part of the first culture is diluted x times to arrive at a first cell density of infected McCoy cells, whereafter the infected McCoy cells comprised in the said another part, are grown to arrive at a cell density which is at least x times higher then the first cell density, before the said at least part of the second culture is harvested. This way, it can be assured that the steps can be repeated over and over again (n times, n being a natural number) without ever needing to re-start the cultivation with fresh (uninfected) McCoy cells and a fresh inoculum of *Lawsonia intracellularis* bacteria.

In an alternative embodiment of the use of persistently infected McCoy cells, the use comprises the steps of growing the persistently infected McCoy cells in a suitable medium at an oxygen concentration less than 18% to arrive at a first culture of McCoy cells infected with *Lawsonia intracellularis* bacteria, having at least a predetermined density of infected McCoy cells, passing a part of the first culture to fresh medium, growing the infected McCoy cells contained in the said part at an oxygen concentration less than 18%, to arrive at a second culture of infected McCoy cells and harvesting the second culture to obtain the *Lawsonia intracellularis* bacteria contained therein, adding fresh medium to a remaining part of the first culture, and growing the infected McCoy cells contained in that remaining part of the culture at an oxygen concentration less than 18%, to arrive at a culture which has at least substantially the same predetermined density of infected McCoy cells as the first culture. In this method, firstly a culture of infected McCoy cells is being obtained having at least a predetermined density of infected cells. This culture is being used more or less as a stand-by or "mother"—culture. A part of this mother culture is then cultivated off-line in a separate cultivation vessel, by passing the infected McCoy cells to fresh medium contained in this vessel. Then the infected McCoy cells are grown in this vessel, for example until growth of the *Lawsonia intracellularis* bacteria has reached a maximum. After that, the contents of this vessel are harvested to obtain purified *Lawsonia intracellularis* bacteria. In the mean time, the infected McCoy cells in the mother culture are also passed by adding fresh media and the infected McCoy cells are re-grown until at least substantially the same density of infected McCoy cells is reached which the mother culture had before the above mentioned part was passed to the separate vessel. Then, a second part of this mother culture can be passed to the separate vessel to obtain a new batch of *Lawsonia intracellularis* bacteria. In an embodiment the second culture (i.e. the culture in the separate vessel) is harvested in a phase wherein the number of viable infected McCoy cells is decreasing. Applicant surprisingly found that the number of *Lawsonia* bacteria may still increase significantly even in a situation wherein the McCoy cells ultimately lose viability. Thus, by leaving the McCoy cells in the separate vessel until a phase wherein they lose viability, the *Lawsonia intracellularis* yield may be significantly increased.

It is noted that the present invention also could enable the cultivation of *Lawsonia intracellularis* in a so-called continuously stirred tank reactor or chemostat. In such a system, a reactor containing McCoy cells persistently infected with *Lawsonia intracellularis* bacteria, could be continuously supplied with fresh media, and on the other hand, there could be a continuous harvest of infected McCoy cells by extracting a flow of the mixed contents of the reactor. Such a system is hitherto unknown for the cultivation of *Lawsonia intracellularis*.

In an embodiment of any of the uses of the newly found persistently infected McCoy cells described supra, passing takes place when the infected McCoy cells are in a growth phase, preferably an exponential growth phase. Preferably the McCoy cells are kept in suspension while growing. The latter is favoured significantly when the $Ca^{2+}$ concentration in the medium is less than 0.3 mmol/l. When this concentration is above 0.3 mmol/l the McCoy cells tend to adhere to available surface or form big lumps in the suspension vessel.

As noted hereinbefore, the present invention also pertains to a McCoy cell line which is persistently infected with *Lawsonia intracellularis* bacteria.

EXAMPLES OF THE INVENTION

Example 1

In this example, McCoy cells persistently infected with *Lawsonia intracellularis* are obtained by infecting adherent McCoy cells (fresh and uninfected), growing them in an adherent state and passing part of the grown culture to fresh medium whereafter the infected cells are regrown. For this experiment one-day old McCoy cells (ATCC CRL 1696, lot 194167) were used, which cells were seeded in a T75 (75 $cm^2$ surface available) flask (Becton Dickinson Falcon, 0.2 m vented blue plug seal cap) at a density of $0.1\times10^5$ cells/$cm^2$. *Lawsonia* bacteria were isolated from a pig of US origin suffering from porcine proliferative enteropathy, concentrated and resuspended in SPG plus 10% FBS in line with art known methods to arrive at a *Lawsonia* inoculum. The medium used for culturing the cells and bacteria is a 1:1 mixture of Minimum Essential Medium Eagle (MEME) and Glasgow Modified Eagle's Medium (GMEM) supplemented with Tryptose phospate broth 0.083% (w/v), Tryptose 0.1% (w/v), Lactalbumin hydrolysate 0.12% (w/v), Sodium Hydrogen Carbonate 0.000245% (w/v) and 10% (v/v) fetal bovine serum (FCS). Percentages are in "volume" unless otherwise indicated.

The McCoy cells are incubated in the T75 flask at 37° C. in an atmosphere of 8% $O_2$, 8% $CO_2$ and $N_2$ for one hour. Medium is added to reach a volume of 25 ml. After that, 0.3 ml of the *Lawsonia* inoculum is added to infect the McCoy cells. This mixture is incubated for seven days in an atmosphere provided by the use of a Campypack Gaspack (Becton Dickinson; the atmosphere will thus contain 5-12% carbon dioxide, 5-15% oxygen, hydrogen and nitrogen) to enable McCoy cells infected with *Lawsonia* bacteria to grow. After seven days, infected McCoy cells are released from the bottom of the flask, and these infected cells are seeded at a density of $0.1\times10^5$ cells/cm$^2$ in a new T75 flask to which 25 ml of the same medium is added. These cells are grown under the same circumstances as mentioned here-above for the first incubation of 7 days. The results are mentioned here-below (Table 1).

TABLE 1

Results of passing to fresh medium to obtain persistently infected McCoy cells

| | McCoy density at start [$10^5$ cells/cm$^2$] | McCoy density at end [$10^5$ cells/cm$^2$] | Percentage infected McCoy cells |
|---|---|---|---|
| First incubation (day 0-7) | 0.1 | 1.9 | 60 |
| Second incubation (day 7-14) | 0.1 | 2.4 | 90 |

It appears that the consecutive incubation under conditions that favour growth of the McCoy cells as well as the *Lawsonia* bacteria, leads to 90% of the McCoy cells being infected. These cells were used as a basis for further experiments described here-beneath which confirm that these cells are persistently infected.

Example 2

In this experiment the persistently infected McCoy cells obtained via the method as described in Example 1 were passed a number of times to new T75 flasks. Each time, the infected cells were re-seeded at a density of $0.1\times10^5$ cells/cm$^2$. Other circumstances were kept the same as in example 1, except that the medium was changed to DMEM supplemented with 10% FCS after six passages. The results are indicated below in Table 2.

It is noted that the antigenic mass (AM) of the *Lawsonia* bacteria was established using an ELISA test. Although the AM at least corresponds to the number of *Lawsonia* bacteria grown in the infected McCoy cells, it is believed that the $TCID_{50}$ better corresponds to the number of viable *Lawsonia* bacteria. The latter measure is established as follows: McCoy cells were grown in a 96-wells dish (Greiner), at $2\times10^4$ cells/ml, 0.1 ml/well for one day. *Lawsonia* harvest (supernatant plus cells) was diluted $10^1$ to $10^8$ times in DMEM+3.7 g/L sodium bicarbonate supplemented with 10% (v/v) FCS, whereafter 100 µl was added per well. Plates were incubated for 7 days at 37° C. in an 8% $CO_2$, 8% $O_2$ and 3.1% $H_2$ atmosphere. Infection was analyzed using immunofluorescence. Titers were calculated using the Reed & Munch method. "ND" means that the respective figure was not determined (for example because of a practical failure or change of routine determinations)

TABLE 2

| Passage | McCoy density at end of passage [$10^5$ cells/cm$^2$] | Antigenic Mass [relative amount] | $TCID_{50}$ [$^{10}$log] |
|---|---|---|---|
| 1 | 4.0 | 77 | 4.7 |
| 2 | 3.3 | 180 | 4.7 |
| 3 | 3.0 | ND | 5.0 |
| 4 | ND | 966 | 5.3 |
| ... | ... | ... | ... |
| 27 | 1.4 | ND | 5.7 |
| 28 | 1.6 | ND | 6.2 |

As can be seen, the infected McCoy cells can be maintained for at least 28 passages without adding fresh cells, merely by passing the infected cells to fresh medium and allowing both the McCoy cells as well as the *Lawsonia* bacteria to grow. At passage 28, the $TCID_{50}$ is still at a high level. This experiment confirms that the McCoy cells are persistently infected with the *Lawsonia* bacteria.

Example 3

In this example an alternative medium was used to show that the present invention does not depend on a particular kind of medium. The medium used is a commonly known glutamine-free DMEM (Gibco), supplemented with 10% FCS and 4 mM L-glutamine. The other circumstances were the same as in Example 2. The results are indicated in Table 3 here-beneath.

TABLE 3

| Passage | McCoy density at end of passage [$10^5$ cells/cm$^2$] | Antigenic Mass [relative amount] | $TCID_{50}$ [$^{10}$log] |
|---|---|---|---|
| 1 | 3.1 | 786 | 5.6 |
| 2 | 3.4 | 2643 | 5.7 |
| 3 | 2.3 | 2618 | 5.3 |
| 4 | 1.4 | 1365 | 4.0 |
| 5 | 1.6 | 1258 | 5.5 |
| 6 | 1.6 | 1690 | 6.1 |
| 7 | 1.3 | 963 | 6.3 |
| 8 | 1.4 | 2511 | 5.9 |

As shown, the McCoy cells remain infected for at least 8 passages in this alternative medium and keep growing at least a factor 13 (up to even a factor 34) after each passage to fresh medium. The antigenic *Lawsonia* mass appears to fluctuate but the tissue culture infectious dose remains at a high level.

Example 4

In this example the medium as used in Example 3 was slightly altered and also the atmospheric conditions were altered to see whether or not this had any significant influence on the cultivation of the persistently infected McCoy cells. The medium was supplemented with 3.3 mM glutathione and the atmosphere was kept at 8% $O_2$, 8% $CO_2$ and $N_2$ qs. Other circumstances were kept the same as in Example 3. The results are indicated here-beneath in Table 4.

TABLE 4

| Passage | McCoy density at end of passage [$10^5$ cells/cm$^2$] | $TCID_{50}$ [$^{10}$log] |
|---|---|---|
| 1 | 2.8 | 5.3 |
| 2 | 3.3 | 5.4 |
| 3 | 2.9 | 5.0 |
| 4 | 2.7 | 5.2 |

Again, the McCoy cells remain infected with *Lawsonia intracellularis* and the infectious dose remains at an adequate level. Adding glutathione appears to have little effect on the growth of the infected cells. Adding cysteine however, surprisingly had a significant effect on the maintenance of persistently infected McCoy cells (data not presented here).

Example 5

In this example a common L-glutamine containing DMEM was used, supplemented with 10% FCS. The atmosphere was the same as used in Example 4. Other circumstances were also the same as in Example 4. This experiment was conducted to verify the results of Example 2 (maintaining the persistently infected McCoy cells for a high number of passages), but under different circumstances. The results are indicated here-beneath in Table 5 (only some intermediate results and the end result are shown).

TABLE 5

| Passage | McCoy density at end of passage [$10^5$ cells/cm$^2$] | $TCID_{50}$ [$^{10}$log] |
|---|---|---|
| 17 | 2.4 | 5.4 |
| ... | ... | ... |
| 27 | 1.4 | 5.7 |
| 28 | 1.6 | 6.2 |
| ... | ... | ... |
| 30 | 2.7 | 5.7 |
| 31 | 3.0 | 6.6 |
| ... | ... | ... |
| 37 | 3.2 | 6.3 |
| 38 | 3.0 | 6.3 |

Again it is shown that the McCoy cells remain infected with *Lawsonia intracellularis* and that the infectious dose remains at an adequate level for a high number of passages.

Example 6

In this example a suspension medium was used to leave the cells in a state in which they do not adhere to the bottom of the T75 flask. The medium consisted of a 1:1 mixture of DMEM-s (DMEM high glucose, not containing L-glutamine, sodium pyruvate and calcium chloride; available from Gibco, art no 21068-028) containing 4 mM L-glutamine and Ex-cell 293 (SAFC Biosciences, cat number 14570). This mixture was supplemented with 10% FCS. The atmosphere in the flasks consisted of 8% $O_2$, 8% $CO_2$, 3.1% $H_2$ and 80.9% $N_2$. Other circumstances were the same as in example 5 (viz. passage of the cells to fresh medium took place every 7 days, cells were seeded at a density of $0.1\times10^5$ cells/cm$^2$). It was confirmed by microscopic examination that the McCoy cells did not adhere to the bottom of the flask and thus were in actual suspension in the medium. The results are indicated here-beneath in Table 6

TABLE 6

| Passage | McCoy density at end of passage [$10^5$ cells/cm$^2$] | AM [—] | $TCID_{50}$ [$^{10}$log] |
|---|---|---|---|
| 1 | 2.8 | 1152 | ND |
| 2 | 1.8 | 383 | ND |
| 3 | 1.8 | 2385 | ND |
| 4 | 1.5 | 398 | 4.7 |
| 5 | 0.8 | 1731 | 6.0 |

TABLE 6-continued

| Passage | McCoy density at end of passage [$10^5$ cells/cm$^2$] | AM [—] | $TCID_{50}$ [$^{10}$log] |
|---|---|---|---|
| 6 | 1.0 | 5420 | ND |
| 7 | 1.0 | 1354 | ND |
| 8 | 1.4 | 4530 | ND |

As can be seen, the McCoy cells after each passage re-grow a factor 8 (up to a factor 28) while remaining infected. The antigenic mass of the *Lawsonia* bacteria fluctuates significantly but in any case, after eight passages the mass is at a level significantly higher then at the starting point. This means that the *Lawsonia* bacteria are viable and grow. The tissue culture infectious dose has been established only at passage 4 and 5 for confirmation purposes. Since the antigenic mass after passage 4 appeared to be relatively low, it was decided to measure the $TCID_{50}$ to confirm that that the culture still contained infectious *Lawsonia intracellularis* bacteria. Indeed, this appeared to be the case. After passage 5, the AM as well as the $TCID_{50}$ were back to a high level. Given the fluctuations observed, it may be that this medium is not ideally suitable for the cultivation of persistently infected McCoy cells in suspension. Still, the cells remain viable and infected throughout the experiment wherein no fresh McCoy cells were added.

Example 7

The experiment of Example 6 is repeated in an atmosphere containing no hydrogen (oxygen and carbon dioxide concentrations are the same as in Example 6). This is to establish whether or not hydrogen indeed can be regarded as being non-essential to maintain McCoy cells persistently infected with *Lawsonia intracellularis*, even when the host cells are in suspension. The results are indicated in Table 7.

TABLE 7

| Passage | McCoy density at end of passage [$10^5$ cells/cm$^2$] | AM [—] |
|---|---|---|
| 1 | 2.4 | 994 |
| 2 | 1.6 | 390 |
| 3 | 3.1 | 687 |
| 4 | 3.1 | 625 |

It appears that the persistently infected McCoy cells ca be maintained in suspension in an atmosphere containing no hydrogen. The cells appear to grow at least a factor 16 in each passage. The *Lawsonia* antigenic mass seems to be somewhat lower then in the experiment according to Example 6, but the number remains at a significant level.

Example 8

In this example it is checked whether the results of Example 7 can be confirmed in a system wherein the persistently infected McCoy cells are in free-floating suspension, in a continuously stirred fermentor. For this, we use a 1250 ml fermentor which is stirred at 250 r.p.m. The medium has a $dO_2$ of 10% and the pH is kept at 7.2 by bubbling carbon dioxide through the medium. The overlay of the fermentor is with nitrogen gas. Gentamycine (40 mg/l) and an anti-foam agent (Dimethicon, 10.5 mg/l, Caldic Netherlands) are added to the medium. The McCoy cells were seeded at $0.3\times10^6$ cells/ml, and passed two times. This way it can be established whether the persistently McCoy cells and the *Lawsonia* infection can be maintained under these circumstances per se. The results are indicated here-beneath in Table 8.

TABLE 8

| Passage | McCoy density at start [$10^6$ cells/$cm^3$] | McCoy density at end [$10^6$ cells/$cm^3$] | $TCID_{50}$ [$^{10}$log] |
|---|---|---|---|
| 1 | 0.3 | 3.3 | 3.6 |
| 2 | 0.3 | 3.0 | 3.5 |

These results indicate that persistently infected McCoy cells can be maintained also in free-floating suspension, even in a medium (atmosphere) containing no hydrogen. The cells at least grow a factor 10 after each passage. The tissue culture infectious dose remains stable which means that the *Lawsonia* infection grows together with the McCoy cells.

Example 9

In this example it is shown that the *Lawsonia* bacteria may continue growing in the McCoy cells even if the viability of the latter cells decreases. For this experiment we use the McCoy cells from passage number 17 of Example 5. These cells are seeded at $0.1\times10^5$ cells/$cm^2$ in a T75 flask in the same medium as used in Example 5. The atmosphere used contains 8% $O_2$, 8% $CO_2$, 3.1% $H_2$ and 80.9% $N_2$. Temperature is 37° C. After passage, the cells are incubated for 14 days without adding fresh medium. At days 7, 8, 11, 12 and 14 the number of viable McCoy cells is determined as well as the *Lawsonia* antigenic mass. The results are indicated here-beneath in Table 9.

TABLE 9

| day | McCoy density at end of day [$10^5$ cells/$cm^2$] | AM [—] |
|---|---|---|
| 7 | 2.9 | 345 |
| 8 | 2.6 | 821 |
| 11 | 2.2 | 2719 |
| 12 | 1.4 | 2659 |
| 14 | 0.5 | 4297 |

It appears that after seven days, the number of viable McCoy cells decrease rapidly. The antigenic mass of *Lawsonia* bacteria however reaches a very high level after 14 days.

The invention claimed is:

1. A method to obtain McCoy cells persistently infected with *Lawsonia intracellularis* bacteria, comprising:

infecting McCoy cells with *Lawsonia intracellularis* bacteria, growing the infected McCoy cells in a suitable medium at an oxygen concentration less than 18% to arrive at a culture of McCoy cells infected with *Lawsonia intracellularis* bacteria, passing at least a part of the said culture to fresh medium; wherein said passing takes place when the infected McCoy cells are in an exponential growth phase; and without adding uninfected McCoy cells to the medium, growing the infected McCoy cells contained in said at least part in the fresh medium at an oxygen concentration less than 18%, to obtain the persistently infected McCoy cells.

2. A method according to claim 1, characterised in that the McCoy cells are grown while being adhered to a surface.

3. A method according to claim 1, characterised in that the McCoy cells are grown while being in suspension.

* * * * *